(12) United States Patent
Young et al.

(10) Patent No.: US 8,409,193 B2
(45) Date of Patent: *Apr. 2, 2013

(54) RF ABLATION PROBES WITH TINE VALVES

(75) Inventors: Kimbolt Young, Newtonville, MA (US); Gerald M. Hubbs, Louisville, KY (US); Steve Pickett, Spencer, IN (US); Gene McCallister, Spencer, IN (US); John Hewitt, Camby, IN (US); Jeffrey W. Zerfas, Bloomington, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 140 days.

This patent is subject to a terminal disclaimer.

(21) Appl. No.: 13/029,863

(22) Filed: Feb. 17, 2011

(65) Prior Publication Data

US 2011/0137310 A1 Jun. 9, 2011

Related U.S. Application Data

(63) Continuation of application No. 11/323,941, filed on Dec. 29, 2005, now Pat. No. 7,896,874.

(51) Int. Cl.
*A61B 18/14* (2006.01)
(52) U.S. Cl. ........................................................ 606/41
(58) Field of Classification Search ............... 606/41
See application file for complete search history.

(56) References Cited

U.S. PATENT DOCUMENTS

| 4,106,512 A | 8/1978 | Bisping |
| 4,217,913 A | 8/1980 | Dutcher |
| 4,311,153 A | 1/1982 | Smits |
| 5,522,875 A | 6/1996 | Gates et al. |
| 5,551,426 A | 9/1996 | Hummel et al. |
| 5,588,960 A | 12/1996 | Edwards et al. |

(Continued)

FOREIGN PATENT DOCUMENTS

| DE | 21 24 684 A1 | 11/1972 |
| EP | 1317908 A A1 | 6/2003 |

(Continued)

OTHER PUBLICATIONS

PCT International Preliminary Report on Patentability (Chapter 1 of the Patent Cooperation Treaty) for PCT/US2005/046699, Applicant: Boston Scientific Scimed, Inc., Form PCT/IB/326 and 373, dated Jul. 19, 2007 (8 pages).

(Continued)

*Primary Examiner* — Lee S Cohen
(74) *Attorney, Agent, or Firm* — Vista IP Law Group LLP

(57) ABSTRACT

A tissue ablation probe is provided. The tissue ablation probe comprises an elongated shaft, at least one electrode tine carried by the elongated shaft, at least one tine exit from which the electrode tine(s) can be deployed from the elongated shaft and retracted within the elongated shaft, and a sheath covering the electrode tine exit(s). The sheath may, e.g., line an exterior surface of the elongated shaft or an interior surface of the elongated shaft. The sheath has at least one tine valve (e.g., a slit) positioned over the electrode tine exit(s) and configured to open when the electrode tine is deployed and to close when the electrode tine(s) is retracted. In one embodiment, the tine valve(s) is configured to open in response to pressure exerted during deployment of the electrode tine(s). In another embodiment, the tine valve(s) is configured to hinder the entry of biological material within the elongated shaft. In one embodiment, the sheath is pliable, such that the tine valve(s) can more easily hinder the entry of the biological material.

17 Claims, 2 Drawing Sheets

U.S. PATENT DOCUMENTS

| | | | |
|---|---|---|---|
| 5,649,975 | A | 7/1997 | Lindegren et al. |
| 5,683,384 | A | 11/1997 | Gough et al. |
| 5,827,276 | A | 10/1998 | LeVeen et al. |
| 5,928,229 | A | 7/1999 | Gough et al. |
| 6,009,877 | A | 1/2000 | Edwards |
| 6,312,429 | B1 | 11/2001 | Burbank et al. |
| 6,379,353 | B1 | 4/2002 | Nichols |
| 6,425,887 | B1 | 7/2002 | McGuckin et al. |
| 6,471,700 | B1 | 10/2002 | Burbank et al. |
| 6,500,175 | B1 | 12/2002 | Gough et al. |
| 6,638,234 | B2 | 10/2003 | Burbank et al. |
| 6,652,520 | B2 | 11/2003 | Moorman et al. |
| 6,989,004 | B2 | 1/2006 | Hinchliffe et al. |
| 7,416,549 | B2 | 8/2008 | Young et al. |
| 7,896,874 | B2 * | 3/2011 | Young et al. ............ 606/41 |
| 2002/0022864 | A1 | 2/2002 | Mahvi et al. |
| 2002/0156472 | A1 | 10/2002 | Lee et al. |
| 2003/0073992 | A1 | 4/2003 | Sliwa et al. |
| 2003/0109870 | A1 | 6/2003 | Lee et al. |
| 2004/0006336 | A1 | 1/2004 | Swanson |
| 2004/0147921 | A1 | 7/2004 | Edwards et al. |
| 2005/0010210 | A1 | 1/2005 | Bee et al. |
| 2005/0059964 | A1 | 3/2005 | Fitz |
| 2005/0080409 | A1 | 4/2005 | Young et al. |
| 2005/0234443 | A1 | 10/2005 | Rioux et al. |
| 2006/0084965 | A1 | 4/2006 | Young |
| 2006/0089635 | A1 | 4/2006 | Young et al. |
| 2006/0149226 | A1 | 7/2006 | McCullagh et al. |
| 2006/0200120 | A1 | 9/2006 | DiCarlo et al. |
| 2007/0161980 | A1 | 7/2007 | Young et al. |

FOREIGN PATENT DOCUMENTS

| | | |
|---|---|---|
| WO | WO 2005048862 | 6/2005 |
| WO | WO 2006036408 | 4/2006 |
| WO | WO 2006049810 A1 | 5/2006 |

OTHER PUBLICATIONS

PCT International Search Report for PCT/US2005/046699, Applicant: Boston Scientific Scimed, Inc., Form PCT/ISA/210 and 220, dated Jul. 6, 2006 (5 pages).

PCT Written Opinion of the International Search Authority for PCT/US2005/046699, Applicant: Boston Scientific Scimed, Inc., Form PCT/ISA/237, dated Jul. 6, 2006 (6 pages).

PCT International Search Report dated Nov. 13, 2007 for related International Application Serial No. PCT/US2006/062105 filed Dec. 14, 2006, Inventor: Kimbolt Young (6 pages).

PCT Written Opinion dated Nov. 13, 2007 for related International Application Serial No. PCT/US2006/062105 filed Dec. 14, 2006, Inventor: Kimbolt Young (6 pages).

* cited by examiner

RF ABLATION PROBES WITH TINE VALVES

CROSS REFERENCE TO RELATED APPLICATIONS

This application is a continuation of U.S. application Ser. No. 11/323,941 filed on Dec. 29, 2005, now issued as U.S. Pat. No. 7,896,874, the disclosure of which is hereby incorporated by reference.

FIELD OF THE INVENTION

The field of the invention relates generally to the structure and use of radio frequency (RF) electrosurgical probes for the treatment of tissue.

BACKGROUND OF THE INVENTION

In oncology, cancer treatment is often performed using radio frequency (RF) ablation techniques. Conventional ablation techniques use an array of RF needles or tines ("tine array"), which may be configured to deploy in a pre-determined shape or pattern for transferring RF energy into surrounding tissue. For example, in an undeployed state, tines are inserted into a target area while housed within the lumen of a cannula. An undeployed tine array enclosed within a cannula may be placed by inserting the cannula through bone and tissue into a target area. Once inserted, the electrode tine array may be deployed by forcing the electrode tines out of a cannula and into the surrounding target tissue. After deployment, RF energy may be transmitted from the electrode tine array to ablate the target tissue, causing heating and eventual necrosis of cancerous or malignant tissue. RF ablation occurs when a high frequency alternating current flows from one electrode to another, completing a current path, causing ionic agitation. Ionic agitation occurs around an active electrode as a result of frictional heating in the tissue surrounding the electrode tines (e.g., electrodes, RF needle probes, and the like) on an array, leading to cell death and necrosis. After ablating the target tissue, the electrode tine array is then retracted into the cannula A need continues for lower profile (smaller gauge) RF probes with larger electrode arrays. In designing for these characteristics, every diminutive amount of space inside the cannula of the RF probe must be utilized. As a result, an electrode array assembly must hold extremely tight clearances and tolerances in concert with the inner diameter of the cannula. Some problems associated with conventional ablation techniques are associated with the deployment of tine arrays. In particular, biological material (e.g., tissue, coagulated blood, and the like) can enter the lumen of a cannula during deployment or retraction. If blood and tissue enters the cannula, mechanical interference (i.e., blockage, jamming, and the like) may result when the electrode tine array is retracted or deployed again. When retracting the electrode tine array, necrosed tissue and blood resulting from the ablation may adhere to the RF needle probes, causing a mechanical interference.

There, thus, remains a need to minimize the entry of biological material into an RF ablation cannula during deployment and/or retraction of electrode tines.

SUMMARY OF THE INVENTION

In accordance with a first aspect of the present inventions, a tissue ablation probe is provided. The tissue ablation probe comprises an elongated shaft, at least one electrode tine carried by the elongated shaft, at least one tine exit from which the electrode tine(s) can be deployed from the elongated shaft and retracted within the elongated shaft, and a sheath covering the electrode tine exit(s). The sheath may, e.g., line an exterior surface of the elongated shaft or an interior surface of the elongated shaft. The sheath has at least one pre-formed tine valve (e.g., a slit) positioned over the electrode tine exit(s) and configured to open when the electrode tine is deployed and to close when the electrode tine(s) is retracted. In one embodiment, the tine valve(s) is configured to open in response to pressure exerted during deployment of the electrode tine(s). In another embodiment, the tine valve(s) is configured to hinder the entry of biological material within the elongated shaft. In one embodiment, the sheath is pliable, such that the tine valve(s) can more easily hinder the entry of the biological material.

In accordance with a second aspect of the present inventions, another tissue ablation probe is provided. The tissue ablation probe comprises an elongated shaft, at least one electrode tine carried by the elongated shaft, at least one tine exit from which the electrode tine(s) can be deployed from the elongated shaft and retracted within the elongated shaft, and a sheath covering the electrode tine exit(s). The sheath may, e.g., line an exterior surface of the elongated shaft or an interior surface of the elongated shaft. The sheath has at least one tine valve positioned over the electrode tine exit(s) and configured to seal over the electrode tine when deployed to hinder the entry of biological material within the elongated shaft. The tine valve(s) may be preformed in the sheath, or alternatively, can be configured to be created upon puncturing of the sheath via deployment of the of electrode tine(s).

The sheath is pliable, such that the tine valve(s) can more easily seal over the electrode tine(s) when deployed and close when the electrode tine(s) are retracted. In one embodiment, the tine valve(s) is configured to close in response to the retraction of the at least one electrode tine into the elongated shaft.

In accordance with a third aspect of the present inventions, still another tissue ablation probe is provided. The tissue ablation probe comprises an elongated shaft, at least one electrode tine carried by the elongated shaft, at least one tine exit from which the electrode tine(s) can be deployed from the elongated shaft and retracted within the elongated shaft, and a sheath covering the electrode tine exit(s). The sheath may, e.g., line an exterior surface of the elongated shaft or an interior surface of the elongated shaft. The sheath is configured to seal over the electrode tine when the electrode tine traverses the sheath to hinder the entry of biological material within the elongated shaft. The sheath is pliable, such that sheath can more easily seal over the electrode tine(s) when deployed. In an optional embodiment, the sheath remains sealed in response to the retraction of the electrode tine(s) into the elongated shaft. In performing the sealing function, the sheath may have at least one pre-formed tine valve that seals over the at least one electrode tine when the electrode tine(s) traverses the sheath, or alternatively, may be configured to puncture when the electrode tine(s) traverses the sheath to seal over the electrode tine(s).

BRIEF DESCRIPTION OF THE DRAWINGS

The drawings illustrate the design and utility of preferred embodiment(s) of the invention, in which similar elements are referred to by common reference numerals. In order to better appreciate the advantages and objects of the invention, reference should be made to the accompanying drawings that illustrate the preferred embodiment(s). The drawings, however, depict the embodiment(s) of the invention, and should not be taken as limiting its scope. With this caveat, the embodiment(s) of the invention will be described and explained with additional specificity and detail through the use of the accompanying drawings in which.

DETAILED DESCRIPTION OF THE ILLUSTRATED EMBODIMENTS

The following described embodiments utilize tine valves that are used to prevent mechanical interferences that may interfere with the deployment or retraction of a tine array. Tine valves secure tine exits, acting as a barrier to prevent or otherwise minimize, filter, reduce, material from entering a cannula during deployment and retraction of a tine array. A covering material (i.e., sheath) may be used to cover the electrode tine exits, enabling the tine valves to open or close when a tine array is deployed or retracted. The tine valves may be preformed within the sheath or can be made when the tine array punctures the sheath. The sheath seals over the electrode tine exits as the electrode tine array is fully retracted into a cannula and opens fully when deploying the electrode tine array. During either retraction or deployment, the sheath also forms a seal and contact with the individual tines of the electrode tine array. The sheath may remove (or minimize, reduce) any material adhering to the electrode tines as the electrode tine array is retracted or prevent (or minimize, reduce) material from entering the cannula. The tine valves prevent (or minimize, reduce) any mechanical interference resulting from material (e.g., necrosed tissue or blood) adhering to individual tines when a tine array is retracted or deployed. Several examples are provided below, but are not limited to only the described implementations.

Figure 1:
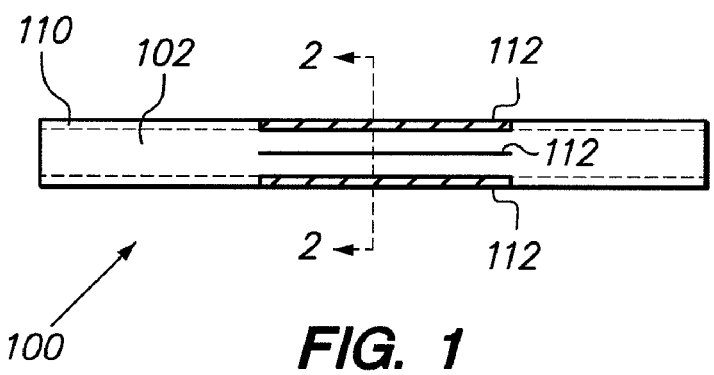
FIG. 1 is a plan view of one embodiment of a tissue ablation probe constructed in accordance with the present inventions, particularly showing a sheath lining an exterior surface of a cannula with closed tine valves and electrode tines retracted within the cannula.
Figure 2:
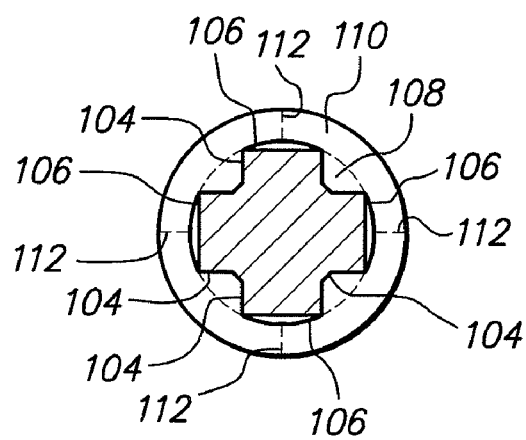
FIG. 2 is a cross-sectional view of the tissue ablation probe of FIG. 1, taken along the line 2-2.

Referring to FIGS. 1-4, an exemplary ablation probe 100 constructed in accordance with one embodiment of the present inventions is described. The ablation probe 100 comprises an elongated cannula 102 and an array of electrode tines 104 (shown in FIGS. 2 and 4) configured to be selectively deployed out of, and retracted within, the cannula 102 via tine exits 106 formed in the side of the cannula 102. In the illustrated embodiment, the elongated cannula 102 is rigid, so that it can be percutaneously introduced through tissue. As shown in FIG. 2, the electrode tines 104, when in a retracted state, reside within an interior 108 of the cannula 102. In the example shown, there are four tines 104 lying within the interior 108 of the cannula 102 and positioned for deployment or retraction through four tine exits 106.

Figure 3:
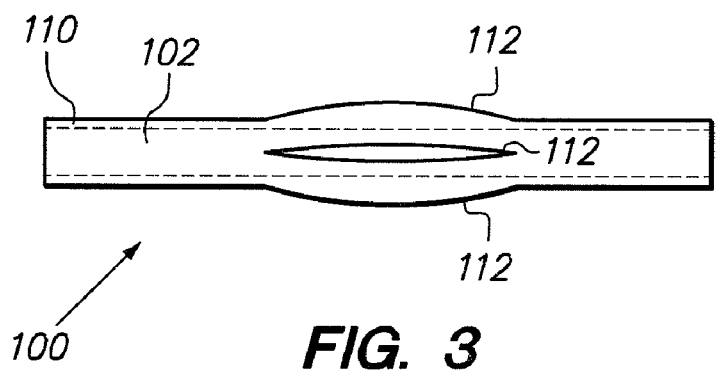
FIG. 3 is a cross-sectional view of the tissue ablation probe of FIG. 1, particularly showing the tine valves opened.

The ablation probe 100 further comprises a sheath 110 with tine valves 112 that provide for the deployment and retraction of the electrode tines 104. The sheath 110 may be a pliable, malleable covering (e.g., Fluorinated Ethylene Propylene (FEP), polyester, rubber, plastic, polyvinyl chloride (PVC), or other similar material) that forms an outer coat or layer over cannula 102. In other examples, sheath 110 may be implemented using a stiff or resistant material. The sheath 110 may be formed onto the surface of the cannula 102 using any suitable technique, such as coating, spraying, electrolysis, etc. In the illustrated embodiments, the tine valves 112 take the form of longitudinal cuts or "slits", which can open, as illustrated in FIG. 3. Alternatively, the tine valves 112 can also be criss-cross shape, horizontal, or shaped to the electrode tine geometry and using the cross section of the electrode tine to act as a plug when retracted. In other examples, tine valves 112 may be implemented as transverse or angled slits in sheath 110. In the illustrated embodiment, the tine valves 112 are preformed within the sheath 110. That is to say, the tine valves 112 exist prior to the initial deployment of the electrode tines 104 from the cannula 102. Alternatively, the tine valves 112 may be created within the sheath 110 as the deployment of the electrode tines 104 punctures the sheath 110.

Figure 4:
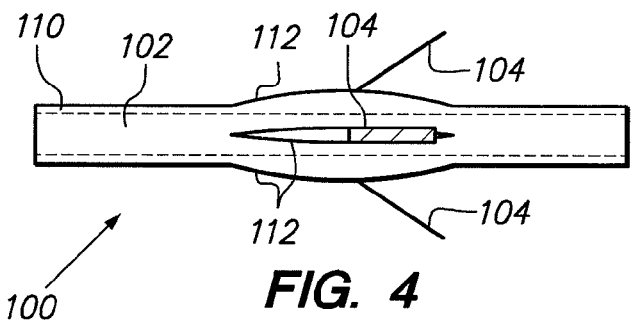
FIG. 4 is a plan view of the tissue ablation probe of FIG. 1, particularly showing the electrode tines deployed from the cannula.

When force is applied, the individual tines 104 are pushed through tine valves 112, which open (or created if not preformed in the sheath 110) in response to the applied pressure of the electrode tines 104 exiting cannula 102, as illustrated in FIG. 4. As the electrode tines 104 are deployed, the pliable, malleable material used for sheath 110 provides a seal around individual tines 104, preventing, or otherwise minimizing or reducing, any biological material from entering cannula 102 through the covered tine exits 106 and into the inside of the cannula 102. As a tine array is retracted, the sides of tine valves 112 contact and provide a seal over tine exits 106. In some examples, sheath 110 may form a hermetic, airtight, non-airtight, full, or partial seal around the electrode tines 104 as they are deployed or retracted. Thus, it can be appreciated that the tine valves 112 prevent mechanical interference with the electrode tine array during either deployment or retraction and reduces the possibility that a tine array may require surgical removal if the electrode tine array is stuck in a deployed or "open" state.

Figure 5:
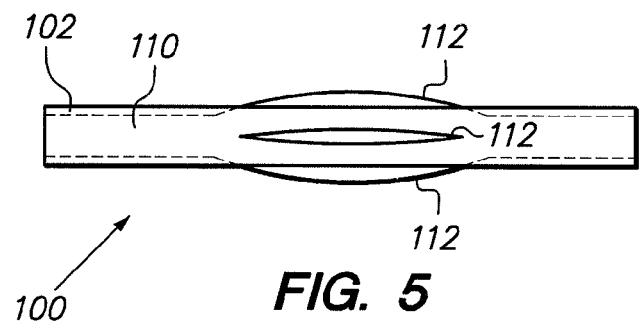
FIG. 5 is a plan view of the tissue ablation probe of FIG. 1, particularly showing a sheath lining an interior surface of the cannula.

In the embodiment illustrated in FIGS. 1-4, the sheath 110 externally covers the cannula 102 and tine exits 106. Alternatively, as illustrated in FIG. 5, the sheath 110 may be located inside of the cannula 102, e.g., as an inner coat or layer within the cannula 102. In this case, the tine valves 112 may, in some examples, protrude or extend through tine exits 106 and cannula 102 as the electrode tines 104 are deployed. Alternatively, a tine valve 112 may not extrude from cannula 116 and, instead, may be forced to one side of a tine exit 106.

Figure 6:
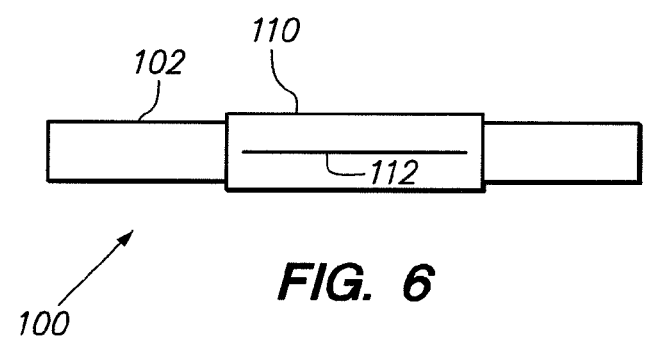
FIG. 6 is a plan view of the tissue ablation probe of FIG. 1, particularly showing the sheath lining the exterior surface along only a portion of the cannula.
Figure 7:
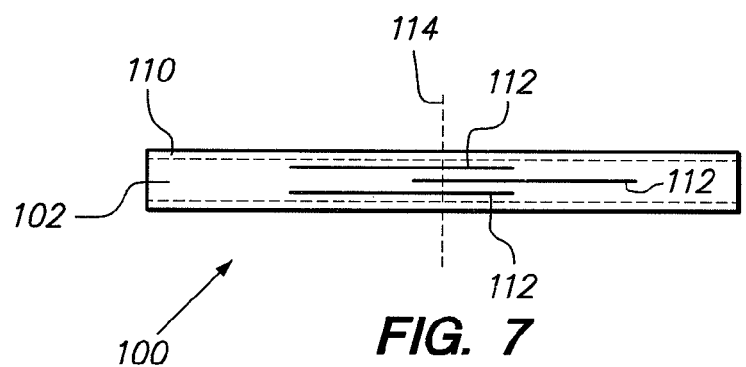
FIG. 7 is a plan view of the tissue ablation probe of FIG. 1, particularly showing offset tine valves.

In the embodiments illustrated in FIGS. 1-5, the sheath 110 extends the entire length of the cannula 102. Alternatively, as illustrated in FIG. 6, the sheath 110 may be configured to cover and overlap the electrode tine exits 106, but not the entire length of cannula 102. In the embodiments illustrated in FIGS. 1-6, the tine valves 112 are aligned around the longitudinal axis of the cannula 102. Alternatively, the tine valves 112 may be positioned at offset intervals relative to a transverse axis 114, as illustrated in FIG. 7. In this case, the electrode tines 104 may be deployed though tine valves 112 at varying intervals, accommodating tine arrays of varying sizes and positions lying within cannula 102. In other examples, several sets of tine valves 112 may be used to accommodate more than one tine array (e.g., a distal and proximal tine arrays).

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed:

1. A tissue ablation probe, comprising:
   an elongated shaft;
   at least one electrode tine carried by the elongated shaft;
   at least one tine exit disposed on the elongated shaft from which the at least one electrode tine can be deployed from the elongated shaft and retracted within the elongated shaft; and
   a sheath covering the at least one electrode tine exit, the sheath configured to puncture and open when the at least one electrode tine is deployed and to close when the at least one electrode tine is retracted, wherein the punctured sheath forms a tine valve at each puncture location.

2. The tissue ablation probe of claim 1, wherein the at least one electrode tine valve is configured to hinder the entry of biological material within the elongated shaft.

3. The tissue ablation probe of claim 1, wherein the sheath lines an exterior surface of the elongated shaft.

4. The tissue ablation probe of claim 1, wherein the sheath lines an interior surface of the elongated shaft.

5. The tissue ablation probe of claim 1, wherein the at least one electrode tine comprises a plurality of electrode tines, and the at least one electrode tine valve comprises a plurality of tine valves.

6. The tissue ablation probe of claim 1, wherein the at least one electrode tine valve is configured to seal over the at least one electrode tine when deployed.

7. The tissue ablation probe of claim 1, wherein the sheath comprises a polymer.

8. A tissue ablation probe, comprising:
   an elongated shaft;
   at least one electrode tine carried by the elongated shaft;
   at least one tine exit disposed on the elongated shaft from which the at least one electrode tine can be deployed from the elongated shaft and retracted within the elongated shaft; and
   a pliable sheath covering the at least one electrode tine exit, the sheath configured to puncture and seal over the at least one electrode tine when deployed to hinder the entry of biological material within the elongated shaft, wherein the punctured sheath forms a tine valve at each puncture location.

9. The tissue ablation probe of claim 8, wherein the sheath lines an exterior surface of the elongated shaft.

10. The tissue ablation probe of claim 8, wherein the sheath lines an interior surface of the elongated shaft.

11. The tissue ablation probe of claim 8, wherein the at least one electrode tine comprises a plurality of electrode tines, and the at least one electrode tine valve comprises a plurality of tine valves.

12. The tissue ablation probe of claim 8, wherein the at least one electrode tine valve is configured to close in response to the retraction of the at least one electrode tine into the elongated shaft.

13. A tissue ablation probe, comprising:
   an elongated shaft;
   at least one electrode tine carried by the elongated shaft;
   at least one tine exit disposed on the elongated shaft from which the at least one electrode tine can be deployed from the elongated shaft and retracted within the elongated shaft; and
   a pliable sheath covering the at least one electrode tine exit, the sheath configured to puncture and seal over the at least one electrode tine when the at least one electrode tine traverses the sheath to hinder the entry of biological material within the elongated shaft.

14. The tissue ablation probe of claim 13, wherein the sheath lines an exterior surface of the elongated shaft.

15. The tissue ablation probe of claim 13, wherein the sheath lines an interior surface of the elongated shaft.

16. The tissue ablation probe of claim 13, wherein the at least one electrode tine comprises a plurality of electrode tines.

17. The tissue ablation probe of claim 13, wherein sheath is configured to remain sealed in response to the retraction of the at least one electrode tine into the elongated shaft.

* * * * *